(12) United States Patent
Zhang et al.

(10) Patent No.: US 10,927,393 B2
(45) Date of Patent: Feb. 23, 2021

(54) NUCLEIC ACID AMPLIFICATIONS

(71) Applicant: Ionian Technologies, LLC, San Diego, CA (US)

(72) Inventors: Honghua Zhang, San Diego, CA (US); Jarrod Provins, Dana Point, CA (US); Richard Roth, Carlsbad, CA (US)

(73) Assignee: Ionian Technologies, LLC, San Diego, CA (US)

( * ) Notice: Subject to any disclaimer, the term of this patent is extended or adjusted under 35 U.S.C. 154(b) by 0 days.

(21) Appl. No.: 13/913,153

(22) Filed: Jun. 7, 2013

(65) Prior Publication Data
US 2013/0330777 A1   Dec. 12, 2013

Related U.S. Application Data

(60) Provisional application No. 61/657,227, filed on Jun. 8, 2012, provisional application No. 61/782,199, filed on Mar. 14, 2013.

(51) Int. Cl.
*C12Q 1/68* (2018.01)
*C12P 19/34* (2006.01)
*C12Q 1/6844* (2018.01)

(52) U.S. Cl.
CPC ............ *C12P 19/34* (2013.01); *C12Q 1/6846* (2013.01)

(58) Field of Classification Search
None
See application file for complete search history.

(56) References Cited

U.S. PATENT DOCUMENTS

| | | | |
|---|---|---|---|
| 5,354,668 A | 10/1994 | Auerbach | |
| 5,455,166 A | 10/1995 | Walker | |
| 5,556,751 A | 9/1996 | Stefano | |
| 5,591,609 A | 1/1997 | Auerbach | |
| 5,614,389 A | 3/1997 | Auerbach | |
| 5,693,517 A * | 12/1997 | Gelfand | C12N 9/1252 |
| | | | 435/193 |
| 5,712,124 A | 1/1998 | Walker | |
| 5,731,150 A | 3/1998 | Sandhu et al. | |
| 5,733,733 A | 3/1998 | Auerbach | |
| 5,744,311 A | 4/1998 | Fraiser et al. | |
| 5,834,202 A | 11/1998 | Auerbach | |

(Continued)

FOREIGN PATENT DOCUMENTS

| AU | 2013228077 | 9/2013 |
|---|---|---|
| EP | 2824189 | 1/2015 |

(Continued)

OTHER PUBLICATIONS

Tan, E. et al. Isothermal DNA amplification coupled with DNA nanospere-based colorimetric detection. Anal.Chem., vol. 77, pp. 7984-7992, 2005.*

(Continued)

*Primary Examiner* — Aaron A Priest
(74) *Attorney, Agent, or Firm* — Casimir Jones, S.C.; Thomas A. Isenbarger

(57) ABSTRACT

A method includes combining a polynucleotide and an amplification reagent mixture to form a reaction mixture, wherein the reaction mixture comprises reversibly bound divalent ions in solution, and adjusting the pH of the reaction mixture to release the reversibly bound divalent ions, thereby initiating amplification of the polynucleotide.

28 Claims, 2 Drawing Sheets

Specification includes a Sequence Listing.

(56) References Cited

U.S. PATENT DOCUMENTS

| | | | |
|---|---|---|---|
| 5,916,779 | A | 6/1999 | Pearson et al. |
| 5,942,391 | A | 8/1999 | Zhang et al. |
| 6,197,557 | B1 * | 3/2001 | Makarov ............... C12Q 1/6855 435/6.1 |
| 6,403,341 | B1 | 6/2002 | Barnes et al. |
| 6,448,065 | B2 | 9/2002 | Laugharn, Jr. et al. |
| 6,566,103 | B2 | 5/2003 | Wijnhoven et al. |
| 7,112,423 | B2 | 9/2006 | Van Ness et al. |
| 7,270,981 | B2 | 9/2007 | Armes et al. |
| 7,399,590 | B2 | 7/2008 | Piepenburg et al. |
| 7,435,561 | B2 | 10/2008 | Piepenburg et al. |
| 7,777,958 | B2 | 8/2010 | Shimmo et al. |
| 9,481,912 | B2 * | 11/2016 | Fischer .................. C12Q 1/686 |
| 2002/0172972 | A1 * | 11/2002 | Tabor ................... C12Q 1/6848 435/6.12 |
| 2003/0082590 | A1 | 5/2003 | Van Ness et al. |
| 2003/0138800 | A1 | 7/2003 | Van Ness et al. |
| 2004/0038213 | A1 | 2/2004 | Kwon |
| 2004/0058378 | A1 | 3/2004 | Kong et al. |
| 2005/0026147 | A1 * | 2/2005 | Walker .................. C12N 9/1252 435/6.1 |
| 2006/0154286 | A1 | 7/2006 | Kong et al. |
| 2008/0038782 | A1 * | 2/2008 | Borns .......................... 435/91.2 |
| 2008/0138878 | A1 * | 6/2008 | Kubu ................... C12Q 1/6848 435/193 |
| 2009/0017453 | A1 | 1/2009 | Maples et al. |
| 2009/0029421 | A1 | 1/2009 | Piepenburg et al. |
| 2009/0081670 | A1 * | 3/2009 | Maples ................. C12Q 1/6844 435/6.12 |
| 2010/0167353 | A1 * | 7/2010 | Walder ................. C12Q 1/6844 435/91.2 |
| 2010/0234245 | A1 | 9/2010 | McGee et al. |
| 2010/0311127 | A1 * | 12/2010 | Piepenburg .......... C12Q 1/6844 435/91.5 |
| 2011/0224105 | A1 * | 9/2011 | Kurn ....................... C12P 19/34 506/26 |
| 2011/0269193 | A1 * | 11/2011 | Rhee .................... C12Q 1/6844 435/91.2 |
| 2012/0077193 | A1 * | 3/2012 | Yamane ................. C12Q 1/686 435/6.11 |
| 2013/0084564 | A1 * | 4/2013 | Mazoyer ............... C12Q 1/6886 435/6.11 |
| 2014/0303000 | A1 * | 10/2014 | Armour ............. C12N 15/1096 506/2 |

FOREIGN PATENT DOCUMENTS

| | | |
|---|---|---|
| GB | 2416352 | 1/2006 |
| JP | 2005-519643 | 7/2005 |
| WO | WO2003/012066 | 2/2003 |
| WO | WO 2004022701 | 3/2004 |
| WO | WO2007/096182 | 8/2007 |
| WO | WO2010141940 | 12/2010 |
| WO | WO2011/085160 | 7/2011 |
| WO | WO2013185081 | 12/2013 |
| WO | WO2015/113828 | 8/2015 |
| WO | WO2016/004333 | 1/2016 |

OTHER PUBLICATIONS

International Preliminary Report in corresponding Application No. PCT/US2013/044796, dated Dec. 18, 2014, pp. 1-9.
Gill et al., "Nucleic acid isothermal amplification technologies: a review," Nucleosides Nucleotides Nucleic Acids 2008 27:224-243.
Mukai et al., "Highly efficient isothermal DNA amplification system using three elements of 5"-DNA-RNA-3" chimeric primers, RNaseH and strand-displacing DNA polymerase," 2007, J. Biochem. 142:273-281.
Van Ness et al., "Isothermal reactions for the amplification of oligonucleotides," PNAS 2003 100:4504-4509.
Tan et al., "Isothermal DNA amplification coupled with DNA nanosphere-based colorimetric detection," Anal. Chem. 2005, 77:7984-7992.
Lizard et al., Nature Biotech. 1998, 6:1197-1202.
Mori et al., "Loop-mediated isothermal amplification (LAMP): a rapid, accurate, and cost-effective diagnostic method for infectious diseases," J. Infect. Chemother. 2009 15:62-69.
Kurn et al., "Novel isothermal, linear nucleic acid amplification systems for highly multiplexed applications," Clin. Chem. 2005, 51:10, 1973-1981.
Piekarowicz et al., "Characterization of the dsDNA prophage sequences in the genome of Neisseria gonorrhoeae and visualization of productive bacteriophage," 2007, BMC Microbiol., 7:66.
Liu et al., 2005, "Rapid identification of *Streptococcus pyogenes* with PCR primers from a putative transcriptional regulator gene," Res. Microbiol., 156:564-567.
Podbielski et al., Molecular characterization of the cfb gene encoding group B streptococcal CAMP-factor, 1994, Med. Microbiol. Immunol., 183:239-256.
Schoenmakers et al., 1992, Biotechniques, 12:870-874.
Fujishiro et al., 1995, Comput. Biol. Med., 25:61-80.
Bahador et al., 2005, Res. J. Agr. Biol. Sci. 1;142-145.
International Search Report and Written Opinion in corresponding Application No. PCT/US13/44796, dated Nov. 8, 2013, pp. 1-7.
El-Harakany AA et al., "Dissociation Constants and Related Thermodynamic Quantities of the Protonated Acid Form of Tris-(Hydroxymethyl)-Aminomethane in Mixtures of 2-Methoxyethanol and Water at Different Temperatures," Journal of Electroanalytical Chemistry:162:285-305 & 296 (1984).
Granholm K. et al., "Desorption of Metal Ions from Kraft Pulps. Part 1. Chelation of Hardwood and Softwood Kraft Pulp With EDTA," Bioresources:5(1)206-226 (2010).
Extended European Search Report in corresponding Application No. 13799829.0, dated Mar. 31, 2016, pp. 1-10.
Arena et al., "Calcium- and Magnesium-EDTA Complexes. Stability Constants and Their Dependence on Temperature and Ionic Strength," Thermochimica Acta, 61 (1983) 129-138.
Examination Report in corresponding Australian Application No. 2013271404, dated Oct. 21, 2016, pp. 1-3.

* cited by examiner

NUCLEIC ACID AMPLIFICATIONS

TECHNICAL FIELD

This disclosure relates to nucleic acid amplifications.

BACKGROUND

Many enzymes, including almost all enzymes that interact with nucleic acids and most proteases, have a requirement for a divalent ion cofactor. For example, enzymes involved in nucleic acid amplification reactions often require divalent magnesium ion (Mg++) as a cofactor.

Nucleic acid amplifications can generate nonspecific amplification products. In many cases, this is due to non-specific oligonucleotide priming and subsequent primer extension events prior to the amplification procedure itself, as the enzymes used are often active at ambient temperature. For example, amplification products due to primer dimerization and subsequent extension are observed frequently. Methods used to overcome this problem include so-called "hot start" reactions, wherein at least one component involved in the amplification reaction (e.g., an enzyme or divalent magnesium ion cofactor) is either separated from the reaction mixture or kept in an inactive state until the temperature of the reaction mixture reaches the appropriate temperature.

SUMMARY

This disclosure is based, at least in part, on the development of methods for control of enzymatic reactions.

This disclosure is also based, at least in part, on the development of methods and compositions for nucleic acid amplification that can provide the advantages of hot start reactions using simple reagents.

In one aspect, the disclosure provides a method comprising: (a) combining a polynucleotide and an amplification reagent mixture to form a reaction mixture, wherein the reaction mixture comprises reversibly bound divalent ions in solution, and (b) adjusting the pH of the reaction mixture to release the reversibly bound divalent ions, thereby initiating amplification of the polynucleotide.

In some embodiments, the divalent ion is selected from the group consisting of: magnesium, calcium, copper, zinc, manganese, iron, cadmium, and lead.

In some embodiments, the divalent ion is magnesium.

In any embodiments of the invention, the amplification reagent mixture may include a pH sensitive chelating agent. The pH sensitive chelating agent may be selected from the group consisting of: ethyleneglycol-bis(2-aminoethylether) tetraacetic acid (EGTA), EGTA derivatives, and EDTA derivatives. Preferably the divalent ions in solution are reversibly bound to the pH sensitive chelating agent. Preferably the pH sensitive chelating agent is ethyleneglycol-bis(2-aminoethylether) tetraacetic acid.

In any embodiments of the invention, the amplification reagent mixture may include a temperature sensitive buffer. In some embodiments, the temperature sensitive buffer may include tris(hydroxymethyl)aminomethane.

In any embodiments of the invention, the pH of the reaction mixture may be adjusted according to the pH of the temperature sensitive buffer.

In any embodiments of the invention, the pH of the reaction mixture may be adjusted by changing the temperature of the reaction mixture from a first temperature to a second temperature.

In any embodiments of the invention, the pKa of the temperature sensitive buffer at the second temperature is at least 0.4 less than the pKa of the temperature sensitive buffer at the first temperature.

In any embodiments of the invention, the temperature sensitive buffer has a ΔpKa of between $-0.04°$ C.$^{-1}$ and $-0.015°$ C.$^{-1}$.

In any embodiments of the invention, the first temperature is between about 0° C. and about 10° C., between about 10° C. and about 20° C., or between about 20° C. and about 30° C. Preferably the first temperature is between about 20° C. and about 30° C.

In any embodiments of the invention, the second temperature is between about 30° C. and about 40° C., between about 40° C. and about 50° C., between about 50° C. and about 60° C., between about 60° C. and about 70° C., between about 70° C. and about 80° C., between about 80° C. and about 90° C., or between about 90° C. and about 100° C. Preferably the second temperature is between about 50° C. and about 60° C.

In specific embodiments of the invention, the first temperature is between about 20° C. and about 30° C. and the second temperature is between about 50° C. and about 60° C.

In any embodiments of the invention, the amplification reagent mixture includes a nicking endonuclease, a DNA or RNA polymerase, a recombinase and/or a reverse transcriptase. In specific embodiments the amplification reagent mixture includes a nicking endonuclease and a DNA or RNA polymerase. In other embodiments the amplification reagent mixture includes a recombinase and a DNA or RNA polymerase. These embodiments may optionally include a reverse transcriptase.

In any embodiments of the invention, the ratio of chelating agent concentration to divalent ion concentration is from about 0.5 to about 2.

In any embodiments of the invention, the free divalent ion concentration at the first temperature is between about 0 and about 10 mM.

In any embodiments of the invention, the free divalent ion concentration at the second temperature is between about 5 mM and about 50 mM.

In any embodiments of the invention, the amplification reagent mixture may comprise one or more components in lyophilized form. In specific embodiments, the amplification reagent mixture may comprise a magnesium salt in lyophilized form. The lyophilized magnesium salt may be reconstituted in a buffer to form magnesium ions in solution. In other embodiments, the amplification reagent mixture may comprise a pH sensitive chelating agent in lyophilized form. The lyophilized pH sensitive chelating agent may be reconstituted in a buffer. According to these embodiments, the buffer may be a temperature sensitive buffer. In some embodiments, the magnesium ions in solution are reversibly bound to a pH sensitive chelating agent. According to any of the foregoing embodiments, the pH of the buffer is operable for the pH sensitive chelating agent to reversibly bind the free magnesium ions in solution. Preferably, the amplification reagent mixture comprises magnesium ions in solution reversibly bound to a pH sensitive chelating agent, wherein the magnesium ions in solution are formed from reconstitution of a lyophilized magnesium salt in a temperature sensitive buffer.

In any embodiments of the invention, amplification of the polynucleotide may occur under substantially isothermal conditions.

In any embodiments of the invention, the polynucleotide is not denatured prior to combining with the amplification reagent mixture.

In any embodiments of the invention, the step of combining is performed at a temperature between about 0° C. and about 10° C., between about 10° C. and about 20° C., or between about 20° C. and about 30° C. Preferably the step of combining is performed at a temperature between about 20° C. and about 30° C.

In any embodiments of the invention, amplification of the polynucleotide does not occur until the temperature of the reaction mixture is between about 30° C. and about 40° C., between about 40° C. and about 50° C., between about 50° C. and about 60° C., between about 60° C. and about 70° C., between about 70° C. and about 80° C., between about 80° C. and about 90° C., or between about 90° C. and about 100° C. Preferably amplification of the polynucleotide does not occur until the temperature of the reaction mixture is between about 50° C. and about 60° C.

In any embodiments of the invention, amplification of the polynucleotide may occur without repeated cycling of the temperature of the reaction mixture between a first temperature and a second temperature.

In any embodiments of the invention, one or more components of the amplification reagent mixture may be provided in a container suitable for use in a fluidic device, cartridge, or lateral flow device.

In any embodiments of the invention, amplification of the polynucleotide may occur without additional reagents added to the reaction mixture formed in the combining step (a).

In any embodiments of the invention, the method may further include the step (c): detecting the amplified polynucleotides. In a further embodiment of the method including the step (c), detecting the amplified polynucleotides may occur without additional reagents added to the reaction mixture formed in the combining step (a).

In any embodiments of the invention, at least 50%, at least 60%, at least 70%, at least 80%, at least 90%, at least 95%, or substantially all the divalent ions in the reaction mixture are in soluble form. In further embodiments, the divalent ions are reversibly bound to a pH sensitive chelating agent. In further embodiments, the divalent ions comprise free divalent ions. In other embodiments, the divalent ions comprise both bound and free divalent ions.

In any embodiments of the invention, the divalent ions in solution are not formed from dissolution of a precipitate.

In any embodiments of the invention, less than 20%, less than 15%, less than 10%, less than 5%, less than 1%, or substantially none of the divalent ions form precipitates prior to amplification of the polynucleotide.

In a further embodiment of the method including the step (c), less than 20%, less than 15%, less than 10%, less than 5%, less than 1%, or substantially none of the divalent ions form precipitates prior to detection of the amplified polynucleotides.

In any embodiments of the invention, the reaction mixture does not include divalent ions bound in precipitated form.

In any embodiments of the invention, the polynucleotide is not pre-heated, for example to a temperature above 30° C., above 40° C., above 50° C., or above 60° C. prior to the combining step (a).

In any embodiments of the invention, the amplification reagent mixture is not pre-heated, for example to a temperature above 30° C., above 40° C., above 50° C., or above 60° C. prior to the combining step (a).

In any embodiments of the invention, the temperature of the amplification reagent mixture that is combined with the polynucleotide in step (a) is between about 0° C. and about 10° C., between about 10° C. and about 20° C., or between about 20° C. and about 30° C. Preferably the temperature of the amplification reagent mixture that is combined with the polynucleotide in step (a) is between about 20° C. and about 30° C.

In another aspect, the disclosure provides a method comprising: (a) combining a polynucleotide and an amplification reagent mixture to form a reaction mixture, wherein the amplification reagent mixture comprises reversibly bound magnesium ions in solution, a temperature sensitive buffer and a pH sensitive chelating agent; and (b) adjusting the temperature of the reaction mixture from (i) a first temperature at which the pH of the temperature sensitive buffer is operable for the pH sensitive chelating agent to reversibly bind the free magnesium ions in solution, such that amplification of the polynucleotide is inhibited, to (ii) a second temperature at which the pH of the temperature sensitive buffer is operable to release the bound magnesium ions from the pH sensitive chelating agent, such that amplification of the polynucleotide can proceed, thereby initiating amplification of the polynucleotide.

In any embodiments of the foregoing method, the pH sensitive chelating agent may be selected from the group consisting of: ethyleneglycol-bis(2-aminoethylether) tetraacetic acid, EGTA derivatives, and EDTA derivatives. Preferably the pH sensitive chelating agent is ethyleneglycol-bis(2-aminoethylether) tetraacetic acid.

In any embodiments of the foregoing method, the temperature sensitive buffer may include tris(hydroxymethyl) aminomethane.

In any embodiments of the foregoing method, the pKa of the temperature sensitive buffer at the second temperature is at least 0.4 less than the pKa of the temperature sensitive buffer at the first temperature.

In any embodiments of the foregoing method, the temperature sensitive buffer has a ΔpKa of between $-0.04°$ $C.^{-1}$ and $-0.015°$ $C.^{-1}$.

In any embodiments of the foregoing method, the first temperature is between about 0° C. and about 10° C., between about 10° C. and about 20° C., or between about 20° C. and about 30° C. Preferably the first temperature is between about 20° C. and about 30° C.

In any embodiments of the foregoing method, the second temperature is between about 30° C. and about 40° C., between about 40° C. and about 50° C., between about 50° C. and about 60° C., between about 60° C. and about 70° C., between about 70° C. and about 80° C., between about 80° C. and about 90° C., or between about 90° C. and about 100° C. Preferably the second temperature is between about 50° C. and about 60° C.

In any embodiments of the foregoing method, the amplification reagent mixture may include a nicking endonuclease, a DNA or RNA polymerase, a recombinase, and/or a reverse transcriptase. In specific embodiments, the amplification reagent mixture includes a nicking endonuclease and a DNA or RNA polymerase. In other embodiments the amplification reagent mixture includes a recombinase and a DNA or RNA polymerase. These embodiments may optionally include a reverse transcriptase.

In any embodiments of the foregoing method, the ratio of chelating agent concentration to magnesium ion concentration is from about 0.5 to about 2.

In any embodiments of the foregoing method, the free magnesium ion concentration at the first temperature is between about 0 and about 10 mM.

In any embodiments of the foregoing method, the free magnesium ion concentration at the second temperature is between about 5 mM and about 50 mM.

In any embodiments of the foregoing method, the amplification reagent mixture may comprise one or more components in lyophilized form. In specific embodiments, the amplification reagent mixture comprises a magnesium salt in lyophilized form. The lyophilized magnesium salt may be reconstituted in a buffer to form magnesium ions in solution. In other embodiments, the amplification reagent mixture comprises a pH sensitive chelating agent in lyophilized form. The lyophilized pH sensitive chelating agent may be reconstituted in a buffer. According to these embodiments, the buffer may be a temperature sensitive buffer. In some embodiments, the magnesium ions in solution are reversibly bound to a pH sensitive chelating agent. According to any of the foregoing embodiments, the pH of the buffer is operable for the pH sensitive chelating agent to reversibly bind the free magnesium ions in solution. Preferably, the amplification reagent mixture comprises magnesium ions in solution reversibly bound to a pH sensitive chelating agent, wherein the magnesium ions in solution are formed from reconstitution of a lyophilized magnesium salt in a temperature sensitive buffer.

In any embodiments of the foregoing method, amplification of the polynucleotide may occur under substantially isothermal conditions.

In any embodiments of the foregoing method, the polynucleotide is not denatured prior to combining with the amplification reagent mixture.

In any embodiments of the foregoing method, the step of combining is performed at a temperature between about 0° C. and about 10° C., between about 10° C. and about 20° C., or between about 20° C. and about 30° C. Preferably the step of combining is at a temperature of between about 20° C. and about 30° C.

In any embodiments of the foregoing method, amplification of the polynucleotide does not occur until the temperature of the reaction mixture is between about 30° C. and about 40° C., between about 40° C. and about 50° C., between about 50° C. and about 60° C., between about 60° C. and about 70° C., between about 70° C. and about 80° C., between about 80° C. and about 90° C., or between about 90° C. and about 100° C. Preferably the amplification of the polynucleotide does not occur until the temperature of the reaction mixture is between about 50° C. and about 60° C.

In any embodiments of the foregoing method, amplification of the polynucleotide occurs without repeated cycling of the temperature of the reaction mixture between a first temperature and a second temperature.

In any embodiments of the foregoing method, one or more components of the amplification reagent mixture may be provided in a container suitable for use in a fluidic device, cartridge, or lateral flow device.

In any embodiments of the foregoing method, amplification of the polynucleotide may occur without additional reagents added to the reaction mixture formed in the combining step (a).

In any embodiments of the foregoing method, the method may further include the step (c): detecting the amplified polynucleotides. In further embodiments of the method including the step (c), detecting the amplified polynucleotides may occur without additional reagents added to the reaction mixture formed in the combining step (a).

In any embodiments of the foregoing method, at least 50%, at least 60%, at least 70%, at least 80%, at least 90%, at least 95%, or substantially all the divalent ions in the reaction mixture are in soluble form. In further embodiments, the divalent ions may be reversibly bound to a pH sensitive chelating agent. In further embodiments, the divalent ions may comprise free divalent ions. In other embodiments, the divalent ions may comprise both bound and free divalent ions.

In any embodiments of the foregoing method, the divalent ions in solution are not formed from dissolution of a precipitate.

In any embodiments of the foregoing method, less than 20%, less than 15%, less than 10%, less than 5%, less than 1%, or substantially none of the divalent ions form precipitates prior to amplification of the polynucleotide.

In further embodiments of the foregoing method including the step (c), less than 20%, less than 15%, less than 10%, less than 5%, less than 1%, or substantially none of the divalent ions form precipitates prior to detection of the amplified polynucleotides.

In any embodiments of the foregoing method, the reaction mixture does not include divalent ions bound in precipitated form.

In another aspect, the disclosure provides a composition comprising one or more reagents for nucleic acid amplification and pH-dependent reversibly bound magnesium ions in solution.

In any embodiments of the foregoing composition, the composition may further include a temperature sensitive buffer and a pH sensitive chelating agent. In specific embodiments, the temperature sensitive buffer may include tris(hydroxymethyl)aminomethane. In other specific embodiments, the pH sensitive chelating agent may include ethyleneglycol-bis(2-aminoethylether) tetraacetic acid. Preferably, the composition further includes tris(hydroxymethyl)aminomethane and ethyleneglycol-bis(2-aminoethylether) tetraacetic acid.

In any embodiments of the foregoing composition, the temperature sensitive buffer can have a ΔpKa of between $-0.04°$ C.$^{-1}$ and $-0.015°$ C.$^{-1}$.

In any embodiments of the foregoing composition, the one or more reagents for nucleic acid amplification can include a nicking endonuclease, a DNA or RNA polymerase, a reverse transcriptase, and/or a recombinase. In specific embodiments the one or more reagents includes a nicking endonuclease and a DNA or RNA polymerase. In other embodiments the one or more reagents includes a recombinase and a DNA or RNA polymerase. These embodiments may optionally include a reverse transcriptase.

In any embodiments of the foregoing composition, the one or more reagents for nucleic acid amplification may comprise one or more components in lyophilized form. In specific embodiments, the one or more reagents may comprise a magnesium salt in lyophilized form. The lyophilized magnesium salt may be reconstituted in a buffer to form magnesium ions in solution. In other embodiments, the one or more reagents may comprise a pH sensitive chelating agent in lyophilized form. The lyophilized pH sensitive chelating agent may be reconstituted in a buffer. According to these embodiments, the buffer may be a temperature sensitive buffer. Preferably, the foregoing composition comprises pH-dependent reversibly bound magnesium ions in solution, wherein the magnesium ions in solution are formed from reconstitution of a lyophilized magnesium salt in a temperature sensitive buffer.

In any embodiments of the foregoing composition, the magnesium ions in solution are not formed from dissolution of a precipitate.

In any embodiments of the foregoing composition, the composition does not comprise magnesium ions bound in precipitated form.

In any embodiments of the foregoing composition, one or more components are provided in a container suitable for use in a fluidic device, cartridge, or lateral flow device.

In another aspect, the disclosure provides a composition comprising one or more reagents for nucleic acid amplification, a temperature sensitive buffer, a pH sensitive chelating agent, and a magnesium salt.

In any embodiments of the foregoing composition, the temperature sensitive buffer can include tris(hydroxymethyl)aminomethane.

In any embodiments of the foregoing composition, the temperature sensitive buffer can have a ΔpKa of between $-0.04°$ $C.^{-1}$ and $-0.015°$ $C.^{-1}$.

In any embodiments of the foregoing composition, the pH sensitive chelating agent can include ethyleneglycol-bis(2-aminoethylether) tetraacetic acid.

Preferably, the composition includes tris(hydroxymethyl) aminomethane and ethyleneglycol-bis(2-aminoethylether) tetraacetic acid.

In any embodiments of the foregoing composition, the one or more reagents for nucleic acid amplification may comprise a nicking endonuclease, a DNA or RNA polymerase, a reverse transcriptase, and/or a recombinase. In specific embodiments the one or more reagents includes a nicking endonuclease and a DNA or RNA polymerase. In other embodiments the one or more reagents includes a recombinase and a DNA or RNA polymerase. These embodiments may optionally include a reverse transcriptase.

In any embodiments of the foregoing composition, the one or more reagents may comprise one or more components in lyophilized form. In specific embodiments, the one or more reagents may comprise a magnesium salt in lyophilized form. The lyophilized magnesium salt may be reconstituted in a buffer to form magnesium ions in solution. In other embodiments, the one or more reagents may comprise a pH sensitive chelating agent in lyophilized form. The lyophilized pH sensitive chelating agent may be reconstituted in a buffer. According to these embodiments, the buffer may be a temperature sensitive buffer. Preferably, the foregoing composition comprises a lyophilized magnesium salt that is reconstituted in a temperature sensitive buffer to form pH-dependent reversibly bound magnesium ions in solution.

In any embodiments of the foregoing composition, the magnesium ions in solution are not formed from dissolution of a precipitate.

In any embodiments of the foregoing composition, the composition does not comprise magnesium ions bound in precipitated form.

In any embodiments of the foregoing composition, one or more components may be provided in a container suitable for use in a fluidic device, cartridge, or lateral flow device.

In yet another aspect, the disclosure provides a method comprising: (a) combining an enzyme and a reagent mixture to form a reaction mixture, wherein the reaction mixture comprises reversibly bound divalent ions in solution, and (b) adjusting the pH of the reaction mixture to release the reversibly bound divalent ions, thereby activating the enzyme.

In any embodiments of the foregoing method, the divalent ion is selected from the group consisting of: magnesium, calcium, copper, zinc, manganese, iron, cadmium, and lead.

In any embodiments of the foregoing method, the reagent mixture may comprise a pH sensitive chelating agent.

In any embodiments of the foregoing method, the reagent mixture may comprise a temperature sensitive buffer.

In any embodiments of the foregoing method, the pH of the reaction mixture can be adjusted according to the pH of the temperature sensitive buffer.

In any embodiments of the foregoing method, the pH of the reaction mixture can be adjusted by changing the temperature of the reaction mixture from a first temperature to a second temperature.

In embodiments of the foregoing method, the enzyme may be a DNA or RNA polymerase.

In any embodiments of the foregoing method, the enzyme may be a nicking endonuclease.

Methods of the invention can include a reaction to amplify the polynucleotide, e.g. under substantially isothermal conditions or not. For example the amplification reactions can include nicking and extension amplification reaction (NEAR), or recombinase polymerase amplification (RPA).

In another aspect, the disclosure features compositions (e.g., dried compositions) that include a nicking endonuclease (e.g., N.BstNBI), a DNA polymerase (e.g., a thermophilic DNA polymerase), and a pH sensitive chelating agent (e.g., EGTA). In some embodiments, the compositions further include a temperature sensitive buffer (e.g., Tris). In embodiments, the compositions further include a reverse transcriptase. In some embodiments, the compositions or methods of the invention can include (i) a forward template that includes a nucleic acid sequence having a recognition region at the 3' end that is complementary to the 3' end of a target sequence antisense strand, a nicking enzyme binding site, a nicking site upstream of the recognition region, and a stabilizing region upstream of said nicking site, and/or (ii) a reverse template that includes a nucleotide sequence having a recognition region at the 3' end that is complementary to the 3' end of a target sequence sense strand (e.g., the complement of the target sequence antisense strand), a nicking enzyme binding site, a nicking site upstream of the recognition region, and a stabilizing region upstream of said nicking site. In some embodiments, the compositions can further include a magnesium salt or magnesium ions.

In some embodiments the compositions or methods of the invention can include one or more nicking enzymes, for example, selected from the group consisting of Nt.BspQI, Nb.BbvCI, Nb.BsmI, Nb.BsrDI, Nb.BtsI, Nt.AlwI, Nt.BbvCI, Nt.BstNBI, Nt.CviPII, Nb.BpuIOI, Nt.BpuIOI, and N.BspD6I. In certain embodiments, the nicking enzyme can be selected from the group consisting of Nt.NBst.NBI, Nb.BsmI, and Nb.BsrDI. Preferably the nicking enzyme is Nt.BstNBI or N.BspD6I. Those of ordinary skill in the art are aware that various nicking enzymes other than those mentioned specifically herein may be used in the methods and compositions of the present invention.

In some embodiments the compositions or methods of the invention can include templates, which can be oligonucleotides that bind to a recognition region of the target and also contain a nicking enzyme binding region upstream of the recognition region and a stabilizing region upstream of the nicking enzyme binding region. The "recognition region" can be a nucleic acid sequence on the template that is complementary to a nucleic acid sequence on the target sequence. The recognition region on the target sequence can be the nucleotide sequence on the target sequence that is complementary to, and binds to, the template. The "stabilizing region" can be a nucleic acid sequence having, for example, about 50% GC content, designed to stabilize the molecule for, for example, the nicking and/or extension reactions.

In yet another aspect, the disclosure features compositions (e.g., dried compositions) that include a recombinase (e.g., UvsX), a DNA polymerase, and a pH sensitive chelating agent (e.g., EGTA). In some embodiments, the compositions further include a temperature sensitive buffer (e.g., Tris). The compositions or methods of the invention can include one or more of (i) a single-stranded DNA binding protein (e.g., gp32), (ii) UvsY, and (iii) a crowding agent (e.g., polyethylene glycol (PEG)). In some embodiments, the compositions can further include a magnesium salt or magnesium ions. In some embodiments the compositions and methods of the invention can preferably comprise engineered and modified analogues of recombinases such as *E. coli* recA and T4 bacteriophage uvsX, polymerases including the *E. coli* DNA polymerase I Klenow fragment, Bst polymerase, Phi-29 polymerase, *Bacillus subtilis* Pol I (Bsu), Pol V, and single-stranded DNA binding proteins from *E. coli* and T4 (e.g. gp32 protein). Labeled probes that are sufficiently complementary and hybridize to polynucleotides or amplified polynucleotide products can be used in any aspects or embodiments of the invention.

In another aspect, a lateral flow device is provided containing polynucleotide amplification reagents such as DNA or RNA polymerases, nicking enzymes, recombinases, and/or reverse transcriptase for nucleic acid amplification, and one or more temperature sensitive pH buffers, one or more pH-sensitive chelating agents, and one or more divalent ions such as magnesium ions and/or one or more divalent metal salts such as a magnesium salt or a magnesium sulfate. In some embodiments one or more of these components can be lyophilized.

In another aspect, a microfluidic device is provided containing polynucleotide amplification reagents such as DNA or RNA polymerases, nicking enzymes, recombinases, and/or reverse transcriptase for nucleic acid amplification, and one or more temperature sensitive pH buffers, one or more pH-sensitive chelating agents, and one or more divalent ions such as magnesium ions and/or one or more divalent metal salts such as a magnesium salt or a magnesium sulfate. In some embodiments one or more of these components can be lyophilized.

In another aspect, a cartridge is provided containing polynucleotide amplification reagents such as DNA or RNA polymerases, nicking enzymes, recombinases, and/or reverse transcriptase for nucleic acid amplification, and one or more temperature sensitive pH buffers, one or more pH-sensitive chelating agents, and one or more divalent ions such as magnesium ions and/or one or more divalent metal salts such as a magnesium salt or a magnesium sulfate. In some embodiments one or more of these components can be lyophilized.

In another aspect, a sample preparation and transfer device is provided containing polynucleotide amplification reagents such as DNA or RNA polymerases, nicking enzymes, recombinases, and/or reverse transcriptase for nucleic acid amplification, and one or more temperature sensitive pH buffers, one or more pH-sensitive chelating agents, and one or more divalent ions such as magnesium ions and/or one or more divalent metal salts such as a magnesium salt or a magnesium sulfate. In some embodiments one or more of these components can be lyophilized.

The methods and compositions described herein can provide for nucleic acid amplification reactions without the need to pre-heat the reaction to a reaction temperature. They also can provide for increased selectivity, sensitivity, and reproducibility of nucleic acid amplification reactions without pre-heating.

In another aspect, the disclosure provides a method comprising: forming a mixture comprising: (a) a sample comprising a target and (b) reagents comprising a binding agent, an ion bound by the binding agent, a buffer, and amplification reagents comprising at least one component having a first activity in the presence of the ion when the ion is bound by the binding agent and a second, different activity in the presence of the ion when the ion is free of the binding agent; and releasing an amount of the ion from the binding agent sufficient to change the activity of the at least one component of the amplification reagents from the first activity to the second activity by increasing a temperature of the mixture from a first temperature to a second temperature.

In any embodiments of the foregoing method, the sample may be a sample, e.g., a liquid such as blood, plasma, serum, sputum, a nasal swab, a vaginal swab, saliva, mucous, or spinal fluid, from a human or animal.

In any embodiments of the foregoing method, the target may be a polynucleotide, e.g., a polynucleotide from a pathogen such as a bacterium or virus. The target, as present in the sample, may be of a double stranded polynucleotide or of a single stranded polynucleotide.

In any embodiments of the foregoing method in which the target is a double stranded polynucleotide, the method may be performed without raising the temperature of the polynucleotide to a temperature sufficient to completely denature more than about 50%, about 35%, about 25%, about 15%, about 7.5%, about 5%, or about 2.5% of the double stranded polynucleotide. For example, the method may be performed without raising the temperature above a temperature at which essentially all of the double stranded polynucleotide remains annealed.

In any embodiments of the foregoing method, the amplification reagents may amplify the target while the activity of the at least one component is in the second state. The step of amplifying may be performed without combining the mixture with additional reagents that participate in amplification and/or detection of the target after the step of forming the mixture.

In any embodiments of the foregoing method, the method may further comprise detecting the presence and/or amount of the target. The detecting may be performed after amplifying an amount of the target by at least about $10^6$ times, e.g., at least about $10^6$ times, at least about $10^7$ times, at least about $10^8$ times, at least about $10^9$ times, at least about $10^{10}$ times, at least about $10^{11}$ times, or at least about $10^{12}$ times.

In any embodiments of the foregoing method that comprise amplifying, at least about 50%, at least about 75%, at least about 90%, at least about 95% or essentially all of the total amount of amplification may be performed when the temperature is at about the second temperature, e.g., within about 15° C. of the second temperature, within about 10° C. of the second temperature, within about 7.5° C. of the second temperature, within about 5° C. of the second temperature, within about 2.5° C. of the second temperature, or at essentially the second temperature.

In any embodiments of the foregoing method, the step of forming the mixture may comprise contacting the sample with the reagents wherein the reagents are in lyophilized form when contacted by the sample.

In any embodiments of the foregoing method that comprise detecting, the step of detecting may be performed in less than about 25 minutes, less than about 20 minutes, or less than about 17.5 minutes after contacting the sample and the reagents. In any embodiments of the foregoing method, the step of forming the mixture may be performed without increasing a temperature of the mixture by more than about 30° C., by more than about 25 degrees, by more than about 20° C., by more than about 15° C., by more than about 10° C., by more than about 5° C. above an ambient temperature adjacent the mixture. For example, the step of forming the mixture may be performed with the reagents at about an ambient temperature adjacent the reagents.

In any embodiments of the foregoing method, the step of forming the mixture may be performed without substantially increasing a temperature of the reagents above a temperature of the reagents immediately prior to the step of forming. The temperature of the reagents immediately prior to the step of forming may be about the same as an ambient temperature surrounding the reagents.

In any embodiments of the foregoing method, the method may be performed without contacting the mixture with (a) with additional reagents that participate in amplification and/or detection of the target or (b) any additional reagents in each case after the temperature of the mixture has been increased above the first temperature.

In any embodiments of the foregoing method, the method may be performed without adding (a) additional reagents that participate in amplification and/or detection of the target or (b) any additional reagents in each case after the step of releasing an amount of ion.

In any embodiments of the foregoing method, the method may be performed without returning the at least one component to the first state from the second state.

In any embodiments of the foregoing method, the method may be performed without simultaneously rebinding more than about 25%, more than about 15%, more than about 10%, or more than about 5% of the released amount of ion.

In any embodiments of the foregoing method, the method may be performed without contacting the sample and/or target with an insoluble precipitate comprising an amount of the ion sufficient to change the activity of the at least one component of the amplification reagents from the first activity to the second activity.

In any embodiments of the foregoing method, the method may be performed without contacting the sample and/or target with an insoluble precipitate comprising an amount of the ion sufficient to change the activity of the at least one component of the amplification reagents from the first activity to the second activity and then dissolving the precipitate.

In any embodiments of the foregoing method, the method may be performed without precipitating more than about 25%, more than about 15 present, more than about 10%, more than about 5%, more than about 2.5% of the released amount of ion from the mixture.

In any embodiments of the foregoing method, the method may be performed without precipitating an amount of the ion sufficient to change the activity of the at least one component of the amplification reagents from the second activity to the first activity.

In any embodiments of the foregoing method, the first temperature may be an ambient temperature adjacent the mixture.

In any embodiments of the foregoing method, the first method may be performed without raising the temperature of the mixture to a temperature greater than 80° C., to a temperature greater than 70° C., to a temperature greater than 65° C., or to a temperature greater than 60° C.

In any embodiments of the foregoing method, the first temperature may be less than about 40° C., less than about 35° C., less than about 30° C., or less than about 27.5° C.

In any embodiments of the foregoing method, the second temperature may be at least about 40° C., at least about 45° C., at least about 50° C., or at least about 55° C.

In any embodiments of the foregoing method, the second temperature may be less than about 75° C., less than about 67.5° C., less than about 62.5° C., less than about 60° C., or about 56.5 degrees or less.

In any embodiments of the foregoing method that comprise detecting, the detecting may be performed when the temperature is at about the second temperature, e.g., within about 15° C. of the second temperature, within about 10° C. of the second temperature, within about 7.5° C. of the second temperature, within about 5° C. of the second temperature, within about 2.5° C. of the second temperature, or at essentially the same temperature.

In any embodiments of the foregoing method, the method may be performed without cycling the temperature of the mixture between the first and second temperatures.

In any embodiments of the foregoing method, the method may be performed without cycling the temperature of the mixture between a lower temperature at which double stranded polynucleotides present in the mixture are substantially annealed and a second temperature at which double stranded polynucleotides present in the mixture are substantially denatured.

In any embodiments of the foregoing method, the steps of forming and combining may be performed within a fluidic network within a housing. The housing may be portable, e.g., handheld. The housing may be a single use housing comprising the reagents stored therein and the first method may comprise introducing the sample into the fluidic network of the housing. The housing may comprise an internal power supply such as a battery and a heater powered by the battery and sufficient to raise the temperature of the mixture to the second temperature.

In any embodiments of the foregoing method, the reagents may be lyophilized prior to forming the mixture.

In any embodiments of the foregoing method, the binding agent may be a pH sensitive binding agent and the buffer may be a temperature sensitive buffer wherein increasing a temperature of the mixture from the first temperature to the second temperature changes the buffering capability of the buffer so that the pH of the mixture changes from a first pH to a second, different pH and wherein the binding agent releases the sufficient amount of the ion at the second pH.

In any embodiments of the foregoing method, the at least one component may be an enzyme such as a DNA polymerase, an RNA polymerase, a nicking endonuclease, or a recombinase. For example, the enzyme may be a nicking enzyme such as Nt.BstNBI or N.BspD6I.

In any embodiments of the foregoing method, the binding agent may be a chelator such as ethyleneglycol-bis(2-aminoethylether) tetraacetic acid, EGTA derivatives, and EDTA derivatives. In any of the foregoing method embodiments, the ion may be magnesium, calcium, copper, zinc, manganese, iron, cadmium, and lead. In any of the foregoing method embodiments, the buffer may be tris(hydroxymethyl)aminomethane. In any of the foregoing method embodiments, the amplification reagents may comprise an amount of reagents sufficient to amplify the target by NEAR. For example, the chelator may be ethyleneglycol-bis(2-aminoethylether) tetraacetic acid, the ion may be magnesium, the buffer may be tris(hydroxymethyl)aminomethane, the at least one component may be a DNA polymerase, an RNA polymerase, Nt.BstNBI or N.BspD6I and the amplification reagents may comprise an amount of reagents sufficient to amplify the target by NEAR.

In any embodiments of the foregoing method, the activity of the at least one component is at least about 10 times higher in the presence of the released amount of ion than when the amount of ion is bound by the binding agent, at least about 20 times higher in the presence of the released amount of ion than when the amount of ion is bound by the binding agent, at least about 50 times higher in the presence of the released amount of ion than when the amount of ion is bound by the binding agent, or at least about 100 times higher in the presence of the released amount of ion than when the amount of ion is bound by the binding agent. The activity may be with respect to amplification of the target.

In any embodiments of the foregoing method in which the target is amplified, the rate of amplification may be at least about 10 times higher in the presence of the released amount of ion than if the amount of ion was bound by the binding agent, at least about 20 times higher in the presence of the released amount of ion than if the amount of ion was bound by the binding agent, at least about 50 times higher in the presence of the released amount of ion than if the amount of ion was bound by the binding agent, or at least about 100 times higher in the presence of the released amount of ion than if the amount of ion was bound by the binding agent.

In any embodiments of the foregoing method in which the target is amplified, the rate of amplification may be at least about 10 times higher when the at least one component is in the second state as compared to when the first component was in the first state, at least about 20 times higher when the at least one component is in the second state as compared to when the first component was in the first state, at least about 50 times higher when the at least one component is in the second state as compared to when the first component was in the first state, or at least about 100 times higher when the at least one component is in the second state as compared to when the first component was in the first state.

In any embodiments of the foregoing method that comprise amplifying, at least about 50%, at least about 75%, at least about 90% at least about 95% or essentially all of the total amount of amplification may be performed without raising the temperature of the mixture to a temperature at which more than 50%, more than 30%, more than 20%, more than 10%, or more than 5% of double stranded polynucleotides present in the mixture are completely denatured. For example, the first method may be performed by amplifying, at least about 50%, at least about 75%, at least about 90% at least about 95% or essentially all of the total amount of amplification performed without first completely denaturing more than 50%, more than 30%, more than 20%, more than 10%, or more than 5% of double stranded polynucleotides present in the mixture.

All ranges disclosed herein, e.g., as "between X and Y," are inclusive of the endpoints.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
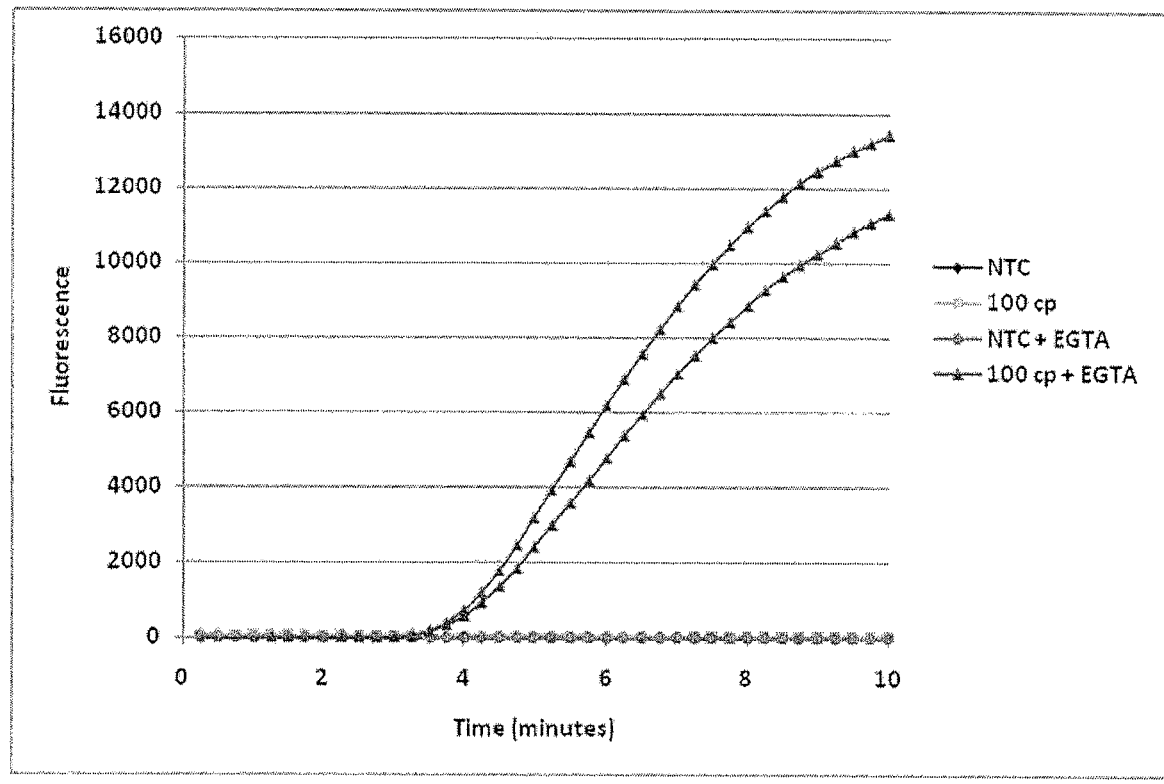
FIG. 1 is a graph depicting fluorescence of NEAR reactions containing no template (NTC), 100 copies of template (100 cp), no template with EGTA (NTC+EGTA), and 100 copies of template with EGTA (100 cp+EGTA).

This disclosure is based, at least in part, on the discovery that the activity of an enzyme that requires a divalent ion cofactor can be controlled by reversibly binding the divalent ions in the reaction mixture. In exemplary methods, a reaction mixture is prepared by combining an enzyme and a reagent mixture, wherein the reaction mixture includes reversibly bound divalent ions in solution. The pH of the reaction mixture may then be adjusted to release the reversibly bound divalent ions, thereby activating the enzyme.

The disclosure is applicable to any reaction involving an enzyme that requires a divalent ion cofactor. Divalent ion cofactors that are essential to enzymes include magnesium, calcium, copper, zinc, manganese, iron, cadmium, and lead.

An exemplary application is in so-called "hot start" reactions, wherein at least one component involved in a reaction (e.g., an enzyme or divalent ion cofactor) is either separated from the reaction mixture or kept in an inactive state until the temperature of the reaction mixture reaches the appropriate temperature.

This disclosure provides for novel "hot start" nucleic acid amplification reactions that include a temperature sensitive buffer and a pH sensitive chelating agent. In exemplary methods, reaction mixtures are prepared at a first temperature (e.g., room temperature) at which the pH of the temperature sensitive buffer is operable for the pH sensitive chelating agent to reversibly bind the free magnesium ions required as cofactors for one or more enzyme components of the reaction, and the progress of the reaction is inhibited. The temperature of the reaction mixture is then adjusted to a second temperature at which the pH of the temperature sensitive buffer is operable to release the bound divalent magnesium ions from the pH sensitive chelating agent, and for the reaction to proceed.

In view of the present disclosure, the person of ordinary skill can select the first temperature, second temperature, the temperature sensitive buffer conditions, and a pH sensitive chelating agent based upon the properties of the specific nucleic acid amplification method used. When elevated reaction temperatures are required, the enzymes used can be derived from a thermophilic species (e.g., *Thermus aquaticus*).

As an example, the nicking and extension amplification reaction (NEAR) can be operated at a temperature of 56° C. The reaction mixture is normally prepared at room temperature and includes a target nucleic acid, oligonucleotides, a DNA polymerase, a nicking endonuclease, tris(hydroxymethyl)aminomethane buffer (pH 8), ethyleneglycol-bis(2-aminoethylether) tetraacetic acid (EGTA), one or more salts (e.g., one or more monovalent and/or divalent magnesium salts), and dNTPs. At this pH, the EGTA binds to the magnesium ions relatively strongly, thus preventing binding of the magnesium ions to the nicking and polymerase enzymes. In general, without magnesium ions the enzymes in the reaction do not display enzymatic activity and the reaction is effectively paused. The temperature is increased to 56° C., at which the pH of the temperature sensitive buffer decreases to less than pH 7.4. At this pH, the effective binding of EGTA to magnesium ions is decreased, resulting in the dissociation of magnesium ions from the EGTA-magnesium complex. The magnesium ions are free to interact with the nicking and polymerase enzymes forming holoenzymes, and the amplification reaction proceeds.

A buffer or buffering agent as used herein is a weak acid or base that can be used to regulate the pH of a solution. Buffers, including buffers that are generally compatible with nucleic acid amplification reactions, are well-known in the art. The pH of many buffers is dependent in part on the temperature of the solution, such that the pH of the buffered solution will vary predictably with temperature. The temperature dependence of tris(hydroxymethyl)aminomethane (Tris) buffer is shown in Table 1.

TABLE 1

Tris buffer temperature pH dependence
pH of Tris buffer (0.05M)

| 5° C. | 25° C. | 37° C. | 56° C. |
|---|---|---|---|
| 7.76 | 7.20 | 6.86 | 6.33 |
| 7.89 | 7.33 | 6.99 | 6.46 |
| 7.97 | 7.41 | 7.07 | 6.54 |
| 8.07 | 7.51 | 7.17 | 6.64 |
| 8.18 | 7.62 | 7.28 | 6.75 |
| 8.26 | 7.70 | 7.36 | 6.83 |
| 8.37 | 7.81 | 7.47 | 6.94 |
| 8.48 | 7.92 | 7.58 | 7.05 |
| 8.58 | 8.02 | 7.68 | 7.15 |
| 8.68 | 8.12 | 7.78 | 7.25 |
| 8.78 | 8.22 | 7.88 | 7.35 |
| 8.88 | 8.32 | 7.98 | 7.45 |
| 8.98 | 8.42 | 8.08 | 7.55 |
| 9.09 | 8.53 | 8.19 | 7.66 |
| 9.18 | 8.62 | 8.28 | 7.75 |
| 9.28 | 8.72 | 8.38 | 7.85 |

Properties of exemplary commercially available buffers 3-{[tris(hydroxymethyl)methyl]amino}propanesulfonic acid (TAPS), glycylglycine,N,N-bis(2-hydroxyethyl)glycine (Bicine), Tris, glycinamide, N-tris(hydroxymethyl)methylglycine (Tricine), 4-2-hydroxyethyl-1-piperazineethane-sulfonic acid (HEPES), 2-{[tris(hydroxymethyl)methyl]amino}ethanesulfonic acid (TES),3-(N-morpholino)propanesulfonic acid (MOPS), N,N-Bis(2-hydroxyethyl)-2-aminoethanesulfonic acid (BES), N-(2-Acetamido)-2-aminoethanesulfonic acid (ACES), piperazine-N,N'-bis(2-ethanesulfonic acid) (PIPES), and 2-(N-morpholino)ethanesulfonic acid (MES) are shown in Table 2.

TABLE 2

Buffer properties

| Common Name | pKa (20° C.) | pKa (25° C.) | pKa (37° C.) | Temp Effect dpKa/dT (1/° C.) | Mol. Weight |
|---|---|---|---|---|---|
| TAPS | 8.49 | 8.40 | 8.18 | −0.018 | 243.3 |
| Glycylglycine | 8.40 | 8.25 | 7.95 | −0.028 | 132.1 |
| Bicine | 8.35 | 8.26 | 8.04 | −0.018 | 163.2 |
| Tris | 8.30 | 8.06 | 7.82 | −0.031 | 121.14 |
| Glycinamide | 8.20 | 8.10 | 7.86 | −0.020 | 110.54 |
| Tricine | 8.15 | 8.05 | 7.79 | −0.021 | 179.2 |
| HEPES | 7.55 | 7.48 | 7.31 | −0.014 | 238.3 |
| TES | 7.50 | 7.40 | 7.16 | −0.020 | 229.20 |
| MOPS | 7.28 | 7.20 | 7.02 | −0.015 | 209.3 |
| BES | 7.17 | 7.09 | 6.90 | −0.016 | 213.25 |
| ACES | 6.90 | 6.78 | 6.56 | −0.020 | 182.2 |
| PIPES | 6.80 | 6.76 | 6.66 | −0.0085 | 302.4 |
| MES | 6.16 | 6.10 | 5.97 | −0.011 | 195.2 |

In some embodiments, the temperature sensitive buffer includes one or more of, e.g., Tricine, Glycinamide, Bicine, Glycylglycine, TES (tris-hydroxymethyl)methyl-amino ethanesulfonic acid), ACES ((N-2-acetomide-2-aminoethanesulfonic acid), and tris(hydroxymethyl)aminomethane.

In some embodiments, the pKa of the temperature sensitive buffer at the second temperature is at least 1, 0.9, 0.8, 0.7, 0.6, 0.5, or 0.4 less than the pKa of the temperature sensitive buffer at the first temperature. In some embodiments, the pH of the reaction mixture at the second temperature is at least 1, 0.9, 0.8, 0.7, 0.6, 0.5, or 0.4 less than the pH of the reaction mixture at the first temperature.

In some embodiments, the temperature sensitive buffer has a ΔpKa (e.g., between the first and second temperatures) of −0.010° C.$^{-1}$ or less, e.g., −0.015° C.$^{-1}$ or less, −0.020° C.$^{-1}$ or less, −0.025° C.$^{-1}$ or less, or −0.030° C.$^{-1}$ or less. In some embodiments, the temperature sensitive buffer has a ΔpKa (e.g., between the first and second temperatures) of between −0.040° C.$^{-1}$ and any one of −0.010° C.$^{-1}$, −0.015° C.$^{-1}$, −0.020° C.$^{-1}$, −0.025° C.$^{-1}$, and −0.030° C.$^{-1}$.

A pH sensitive chelating agent, as used herein, is a chemical that forms soluble complexes with divalent ions, e.g. magnesium ions, such that the divalent ions cannot participate in chemical reactions, e.g., as cofactors of enzymes. Maguire et al., 2002, Biometals, 15:203-210, provides a review of magnesium biochemistry. Many pH sensitive chelating agents that bind magnesium ions are known in the art. Exemplary classes of pH sensitive chelating agents include polyamino-carboxylic acids (e.g., ethylene glycol tetraacetic acid (EGTA), ethylenediaminetetraacetic acid (EDTA), nitrilotriacetic acid (NTA), NTA derivatives, iminodiacetic acid (IDA), IDA derivatives, citric acid, oxalate acid, N-(hydroxyethyl)-ethylenediaminetriacetic acid (HEDTA), and diethyltriaminepentaacetatic acid (DTPA)), azobenzenes (see, e.g., Momotake et al., 2003, Tetrahedron Lett., 44:7277-80), and alkoxyacetic acids (see, e.g., Starek et al., 2006, Acta Pol. Pharm., 63:89-94). Non-limiting examples of pH sensitive chelating agents are described herein. The binding of most pH sensitive chelating agents to magnesium ions is dependent on the pH of the solution. As the pH drops, hydrogen ions successfully compete with magnesium ions for binding to the chelating agent (e.g., the effective stability constant or conditional stability constant of the pH dependent chelating agent and magnesium complex decreases as the pH decreases).

In some embodiments, the pH dependent chelating agent is a monodentate pH dependent chelating agent (e.g., any of the monodentate pH dependent chelating agents described herein or known in the art). In some embodiments, the monodentate pH sensitive chelating agent is citric acid.

In some embodiments, the pH dependent chelating agent is a multidentate pH dependent chelating agent (e.g., any of the multidentate pH dependent chelating agents described herein or known in the art). Multidentate pH sensitive chelating agents usually form more stable magnesium complexes than those formed by similar monodentate pH sensitive chelating agents, and are more pH dependent due to the presence of multiple pH sensitive functional groups. These functional groups form different protonated states as pH changes. As a result the effective stability constant, or conditional stability constant, decreases as the pH decreases. In some embodiments, the multidentate pH sensitive chelating agent contains one or more (e.g., at least two, three, or four) carboxylate and/or amino functional groups (e.g., ethyleneglycol-bis(2-aminoethylether) tetraacetic acid (EGTA), ethylenediaminetetraacetic acid (EDTA), EGTA derivatives, EDTA derivatives, N-methyliminodiacetic acid, nitrilotriacetic acid (NTA), NTA derivatives, DL-2-(2-methylthioethyl)nitriloacetic acid, (2-hydroxytrimethylene)dinitrilotetraacetic acid, DL-1-ethylethylenedinitrilotetraacetic acid N,N-diamide, DL-1-methylethylenedinitrilotetraacetic acid N,N-diamide, ethylenediiminodipropanedioic acid (EDDM), ethylenediiminodi-2-propanoic acid, ethylenediiminodiacetic acid (EDDA), N-(2-pyridylmethyl)iminodiacetic acid, 1,3-phenylenedinitrilotetraacetic acid, ethylenedinitrilotetra(3-propanoic acid), iminodiacetic acid (IDA), IDA derivatives, oxalic acid, o,p-EDDHA (Ethylenediamine-N-(o-hydroxyphenylacetic)-N-(p-hydroxyphenylacetic) acid), o,o-EDDHA, and p,p-EDDHA.

Table 3 shows the logarithms of the magnesium-ligand stability constant and acid dissociation constant of some non-limiting exemplary pH sensitive chelating agents.

tion based on factors such as pH and pH dependent chelating agent concentration are described, e.g., in Schoenmakers et al., 1992, Biotechniques, 12:870-874 and Fujishiro et al., 1995, Comput. Biol. Med., 25:61-80. Versions of such algorithms can be obtained at www.ru.nl/organphy/chelator/Chelmain.html and maxchelator.stanford.edu.

In some embodiments, the ratio of chelating agent concentration to magnesium ion concentration is about 0.1 to 10 (e.g., about 0.1 to 0.5, about 0.2 to 1, about 0.5 to 2, about 1 to 5, or about 2 to 10).

In some embodiments, the free magnesium ion concentration at the first temperature is between about 0 and about 10 mM (e.g., between about 0 and about 0.1 mM, between about 0 and about 0.2 mM, between about 0 and about 0.5

TABLE 3

Logarithms of Magnesium-Ligand Stability Constants and Acid Dissociation Constants for Exemplary Multidentate pH Sensitive Chelating Agents

| pH Sensitive Ligand | log K | pKa1[1] | pKa2 | pKa3 | pKa4 | pKa4 |
|---|---|---|---|---|---|---|
| Ethylenedinitrilotetra (3-propanoic acid) | 1.8[1] | | | | | |
| 1,3-Phenylenedinitrilotetraacetic acid | 2 | | | | | |
| N-(2-Pyridylmethyl)iminodiacetic acid | 4 | | | | | |
| EDDA (Ethylenediiminodiacetic acid) | 4 | | | | | |
| Ethylenediiminodi-2-propanoic acid | 2.8 | | | | | |
| EDDM (Ethylenediiminodipropanedioic acid) | 4.9 | | | | | |
| DL-1-Methylethylenedinitrilotetraacetic acid N,N-diamide | 5.1 | | | | | |
| DL-1-Ethylethylenedinitrilotetraacetic acid N,N-diamide | 4.9 | | | | | |
| (2-Hydroxytrimethylene)dinitrilotetraacetic acid | 5.3 | | | | | |
| DL-2-(2-Methylthioethyl)nitriloacetic acid | 1.5 | | | | | |
| EDTA (Ethylenedinitrilotetraacetic acid) | 8.8 | 1.5 | 2 | 2.69 | 6.13 | 10.4 |
| EGTA (Ethylene bis(oxyethylenenitrilo) tetraacetic acid) | 5.3 | <2 | 2.7 | 8.8 | 9.5 | |
| IDA (Iminodiacetic acid) | 2.9 | 1.8 | 2.6 | 9.5 | | |
| MIDA (N-methyliminodiacetic acid) | 3.4 | 1.4 | 2.1 | 9.6 | | |
| Citric acid | 3.4 | 3.1 | 4.8 | 6.4 | | |
| NTA (nitrilotriacetic acid) | 5.4 | 1.9 | 2.5 | 9.7 | | |

[1]$K_{a1}$ = [HL]/[H$^+$][L], Ka2 = [H$_2$L]/[H$^+$][HL], Ka3 = [H$_3$L]/[H$^+$][H$_2$L], Ka4 = [H$_4$L]/[H$^+$][H$_3$L], Ka5 = [H$_5$L]/[H$^+$][H$_4$L].
[2]The data are compiled from Smith and Martell, 1976 & 2001; 2005 IUPAC, Pure and Applied Chemistry 77, 1445-1495; and Pure Appl. Chem., 1982, Vol. 54, No. 12, pp. 2693-2758.

In some embodiments, the logarithm of the stability constant for the complex of magnesium ion and the pH sensitive chelating agent is between 1 and 9 (e.g., between 2 and 9, between 2 and 6, and between 3 and 6).

In some embodiments, the first temperature is between about 0° C. and about 30° C. (e.g., between about 10° C. and about 30° C., between about 0° C. and about 5° C., between about 5° C. and about 10° C., between about 10° C. and about 15° C., between about 15° C. and about 20° C., between about 20° C. and about 25° C., or between about 25° C. and about 30° C.). In some embodiments, the second temperature is between about 30° C. and about 100° C. (e.g., between about 30° C. and about 40° C., between about 40° C. and about 50° C., between about 50° C. and about 60° C., between about 60° C. and about 70° C., between about 70° C. and about 80° C., between about 80° C. and about 90° C., or between about 90° C. and about 100° C.).

In view of the present disclosure, one of ordinary skill can select a pair of one or more temperature sensitive buffers and one or more pH dependent chelating agents to provide a desired amount of magnesium ion binding at a first temperature and a second temperature such that one or more enzymatic reactions in a nucleic acid amplification reaction are inhibited at the first temperature and permitted at the second temperature. Algorithms to aid in prediction of magnesium ion binding and free magnesium ion concentramM, between about 0 and about 1 mM, between about 0 and about 2 mM, or between about 0 and about 5 mM).

In some embodiments, the free magnesium ion concentration at the second temperature is between about 5 and about 50 mM (e.g., between about 5 and about 10 mM, between about 5 and about 20 mM, between about 10 and about 20 mM, or between about 10 and about 50 mM).

Numerous isothermal nucleic acid amplification techniques are known, including, for example, nicking and extension amplification reaction (NEAR), recombinase polymerase amplification (RPA), isothermal and chimeric primer-initiated amplification of nucleic acids (ICAN), transcription-mediated amplification (TMA), nucleic acid sequence-based amplification (NASBA), signal-mediated amplification of RNA technology (SMART), strand-displacement amplification (SDA), rolling circle amplification (RCAT), ligase amplification reaction, loop-mediated isothermal amplification of DNA (LAMP), isothermal multiple displacement amplification, helicase-dependent amplification (HDA), single primer isothermal amplification (SPIA), and circular helicase-dependent amplification. Polymerase chain reaction and its variants may also be used. These non-isothermal reactions typically use thermal cycling to cause separation of nucleic acid strands. Isothermal and non-isothermal amplification methods are discussed in, for example, Gill et al., Nucleosides Nucleotides Nucleic Acids 2008 27:224-243; Mukai et al., 2007, J. Biochem. 142:273-281; Van Ness et al., PNAS 2003 100:4504-4509; Tan et al., Anal. Chem. 2005, 77:7984-7992; Lizard et al., Nature Biotech. 1998, 6:1197-1202; Mori et al., J. Infect. Chemother. 2009 15:62-69; Notomi et al., NAR 2000, 28:e63; and Kurn et al., Clin. Chem. 2005, 51:10, 1973-1981. Other references for these general amplification techniques include, for example, U.S. Pat. Nos. 7,112,423; 5,455,166; 5,712,124; 5,744,311; 5,916,779; 5,556,751; 5,733,733; 5,834,202; 5,354,668; 5,591,609; 5,614,389; and 5,942,391; and U.S. patent publications numbers US20030082590; US20030138800; US20040058378; US20060154286; US20090081670; and US 20090017453. All of the above documents are incorporated herein by reference.

The amplification reactions above typically use one or more enzymes that require divalent magnesium ions as a cofactor, e.g., DNA polymerases, type II restriction endonucleases (e.g., type IIS or nicking endonucleases), recombinases (e.g., RecA, UvsX), reverse transcriptases, DNA-directed RNA polymerases, RNA-directed RNA polymerases, ribonuclease H enzymes, or DNA ligases. Therefore, the reactions can be inhibited when free magnesium ion is reduced by action of a pH dependent chelating agent.

Amplification reactions provided by this disclosure include those reactions that occur under substantially isothermal conditions. Also included in this disclosure are amplification reactions in which the polynucleotide is not denatured prior to combining with the amplification reagent mixture. Additionally, amplification reactions are provided in which the polynucleotide is amplified without repeated cycling of the temperature of the reaction mixture between a first temperature and a second temperature.

Amplification of the polynucleotide can occur without additional reagents added to the initial reaction mixture formed from combining the polynucleotide with an amplification reagent mixture. The amplified polynucleotides may be detected, also in some cases without additional reagents added to the initial reaction mixture.

NEAR is one exemplary method for isothermal amplification of nucleic acids. The NEAR reaction uses nicking endonucleases (also known as nicking restriction endonucleases or nicking enzymes) in combination with a strand-displacing DNA polymerase to amplify short target sequences. NEAR methods are disclosed, e.g., in US 2009/0017453 and US 2009/0081670, each of which is incorporated herein by reference.

RPA is one exemplary method for isothermal amplification of nucleic acids. RPA employs enzymes known as recombinases that are capable of pairing oligonucleotide primers with homologous sequence in duplex DNA. In this way, DNA synthesis is directed to defined points in a target double-stranded DNA. Using two gene-specific primers, an exponential amplification reaction is initiated if the target sequence is present. The reaction progresses rapidly and results in specific amplification from just a few target copies to detectable levels. RPA methods are disclosed, e.g., in U.S. Pat. Nos. 7,270,981; 7,399,590; 7,777,958; 7,435,561; US 2009/0029421; and WO 2010/141940, all of which are incorporated herein by reference.

The components of an isothermal amplification reaction can be provided in a solution and/or in dried (e.g., lyophilized) form. When one or more of the components are provided in dried form, a resuspension or reconstitution buffer (e.g., a temperature sensitive buffer) can be also be provided.

Based on the particular type of amplification reaction, the reaction mixture can contain buffers (e.g., a temperature sensitive buffer), salts, nucleotides, and other components as necessary for the reaction to proceed.

The magnesium can be provided as a salt, such as magnesium sulfate and magnesium chloride. The magnesium, for example in the form of a salt, can also be provided in a solution and/or in dried (e.g., lyophilized) form. When reconstituted from a buffer, a lyophilized magnesium salt dissociates to form free magnesium ions (Mg++) that are available to act as an enzyme cofactor.

In some embodiments, at least 50%, at least 60%, at least 70%, at least 80%, at least 90%, at least 95%, or substantially all the divalent ions, for example magnesium ions, in the reaction mixture are in soluble form. The solubilized divalent ions can be free or reversibly bound to a pH sensitive chelating agent.

It is known that some divalent ions in solution, for example magnesium ions in solution, can precipitate as solids upon addition of an acid, for example phosphoric acid, to the solution. This precipitation reaction is commonly used in "hot start" PCR to sequester, at room temperature, the magnesium ions that are required for PCR. Upon raising the temperature to 95° C. or higher in the initialization step for PCR, the magnesium precipitates are dissolved, freeing the magnesium ions to act as co-factors for enzymes.

In any of the methods and compositions of the invention, the divalent ions (e.g. magnesium ions) in solution are not formed from dissolution of a precipitate, such as a magnesium precipitate that forms from precipitation of magnesium ions under acidic conditions. In any embodiment of the methods and compositions of the invention, the reaction mixture does not include divalent ions bound in precipitated form. In further embodiments, less than 20%, less than 15%, less than 10%, less than 5%, less than 1%, or substantially none of the divalent ions form precipitates prior to amplification of the polynucleotide. For the purposes of this invention, a component of the reagent mixture that is provided in dried or lyophilized form, such as a magnesium salt that is provided in lyophilized form, is not a precipitate and a lyophilized form is not a precipitated form.

The target nucleic acid can be a nucleic acid present in a mammal (e.g., human), a plant, a fungus (e.g., a yeast), a protozoa, a bacterium, or a virus. For example, the target nucleic acid can be present in the genome of an organism of interest (e.g., on a chromosome) or on an extrachromosomal nucleic acid. In some embodiments, the target nucleic acid is an RNA, e.g., an mRNA. In some embodiments, the target nucleic acid is DNA (e.g., double-stranded DNA). In particular embodiments, the target nucleic acid is specific for the organism of interest, i.e., the target nucleic acid is not found in other organisms or not found in organisms similar to the organism of interest.

The target nucleic acid can be present in a bacteria, e.g., a Gram-positive or a Gram-negative bacteria. Non-limiting exemplary bacterial species include *Acinetobacter* sp. strain ATCC 5459, *Acinetobacter calcoaceticus, Aerococcus viridans, Bacteroides fragilis, Bordetella pertussis, Bordetella parapertussis, Campylobacter jejuni, Clostridium difficile, Clostridium perfringens, Corynebacterium* spp., *Chlamydia pneumoniae, Chlamydia trachomatis, Citrobacter freundii, Enterobacter aerogenes, Enterococcus gallinarum, Enterococcus faecium, Enterobacter faecalis* (e.g., ATCC 29212), *Escherichia coli* (e.g., ATCC 25927), *Gardnerella vaginalis, Helicobacter pylori, Haemophilus influenzae* (e.g., ATCC 49247), *Klebsiella pneumoniae, Legionella pneumophila* (e.g., ATCC 33495), *Listeria monocytogenes* (e.g., ATCC 7648), *Micrococcus* sp. strain ATCC 14396, *Moraxella catarrhalis*, *Mycobacterium kansasii*, *Mycobacterium gordonae*, *Mycobacterium fortuitum*, *Mycoplasma pneumoniae*, *Mycoplasma hominis*, *Neisseria meningitis* (e.g., ATCC 6250), *Neisseria gonorrhoeae*, *Oligella urethralis*, *Pasteurella multocida*, *Pseudomonas aeruginosa* (e.g., ATCC 10145), *Propionibacterium acnes*, *Proteus mirabilis*, *Proteus vulgaris*, *Salmonella* sp. strain ATCC 31194, *Salmonella typhimurium*, *Serratia marcescens* (e.g., ATCC 8101), *Staphylococcus aureus* (e.g., ATCC 25923), *Staphylococcus epidermidis* (e.g., ATCC 12228), *Staphylococcus lugdunensis*, *Staphylococcus saprophyticus*, *Streptococcus pneumoniae* (e.g., ATCC 49619), *Streptococcus pyogenes*, *Streptococcus agalactiae* (e.g., ATCC 13813), *Treponema palliduma*, Viridans group streptococci (e.g., ATCC 10556), *Bacillus anthracis*, *Bacillus cereus*, *Francisella philomiragia* (GAO1-2810), *Francisella tularensis* (LVSB), *Yersinia pseudotuberculosis* (PB 1/+), *Yersinia enterocolitica*, O:9 serotype, and *Yersinia pestis* (P 14−). In some embodiments, the target nucleic acid is present in a species of a bacterial genus selected from *Acinetobacter, Aerococcus, Bacteroides, Bordetella, Campylobacter, Clostridium, Corynebacterium, Chlamydia, Citrobacter, Enterobacter, Enterococcus, Escherichia, Helicobacter, Haemophilus, Klebsiella, Legionella, Listeria, Micrococcus, Mobilincus, Moraxella, Mycobacterium, Mycoplasma, Neisseria, Oligella, Pasteurella, Prevotella, Porphyromonas, Pseudomonas, Propionibacterium, Proteus, Salmonella, Serratia, Staphylococcus, Streptococcus, Treponema, Bacillus, Francisella*, or *Yersinia*. In some embodiments, the target nucleic acid is found in Group A *Streptococcus* or Group B *Streptococcus*.

Exemplary chlamydial target nucleic acids include sequences found on chlamydial cryptic plasmids.

Exemplary *M. tuberculosis* target nucleic acids include sequences found in IS6110 (see U.S. Pat. No. 5,731,150) and/or IS1081 (see, e.g., Bahador et al., 2005, Res. J. Agr. Biol. Sci., 1:142-145).

Exemplary *N. gonorrhea* target nucleic acids include sequences found in NGO0469 (see, e.g., Piekarowicz et al., 2007, BMC Microbiol., 7:66) and NGO0470.

Exemplary Group A *Streptococcus* target nucleic acids include sequences found in Spy1258 (see, e.g., Liu et al., 2005, Res. Microbiol., 156:564-567), Spy0193, lytA, psaA, and ply (see, U.S. Patent Application Publication No. 2010/0234245).

Exemplary Group B *Streptococcus* target nucleic acids include sequences found in the cfb gene (see, e.g., Podbielski et al., 1994, Med. Microbiol. Immunol., 183:239-256).

In some embodiments, the target nucleic acid is a viral nucleic acid. For example, the viral nucleic acid can be found in human immunodeficiency virus (HIV), an influenza virus (e.g., an influenza A virus, an influenza B virus, or an influenza C virus), or a dengue virus. Exemplary HIV target nucleic acids include sequences found in the Pol region.

In some embodiments, the target nucleic acid is a protozoan nucleic acid. For example, the protozoan nucleic acid can be found in *Plasmodium* spp., *Leishmania* spp., *Trypanosoma brucei gambiense, Trypanosoma brucei rhodesiense, Trypanosoma cruzi, Entamoeba* spp., *Toxoplasma* spp., *Trichomonas vaginalis*, and *Giardia duodenalis*.

In some embodiments, the target nucleic acid is a mammalian (e.g., human) nucleic acid. For example, the mammalian nucleic acid can be found in circulating tumor cells, epithelial cells, or fibroblasts.

In some embodiments, the target nucleic acid is a fungal (e.g., yeast) nucleic acid. For example, the fungal nucleic acid can be found in *Candida* spp. (e.g., *Candida albicans*).

Detecting the amplified product in any of the aspects and embodiments of the invention typically includes the use of labeled probes that are sufficiently complementary and hybridize to the amplified product corresponding to the target nucleic acid. Thus, the presence, amount, and/or identity of the amplified product can be detected by hybridizing a labeled probe, such as a fluorescently-labeled probe, that is complementary to the amplified product. In some embodiments, the detection of a target nucleic acid sequence of interest includes the combined use of an isothermal amplification method and a labeled probe such that the product is measured in real time. In another embodiment, the detection of an amplified target nucleic acid sequence of interest includes the transfer of the amplified target nucleic acid to a solid support, such as a membrane, and probing the membrane with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes that are arrayed in a predetermined array with an addressable location and that are complementary to the amplified target nucleic acid.

Typically, one or more primers are utilized in an amplification reaction. Amplification of a target nucleic acid involves contacting the target nucleic acid with one or more primers that are capable of hybridizing to and directing the amplification of the target nucleic acid. In some embodiments, the sample is contacted with a pair of primers that include a forward and reverse primer that both hybridize to the target nucleic.

Real-time amplification monitors the fluorescence emitted during the reaction as an indicator of amplicon production as opposed to the endpoint detection. The real-time progress of the reaction can be viewed in some systems. Typically, real-time methods involve the detection of a fluorescent reporter. Typically, the fluorescent reporter's signal increases in direct proportion to the amount of the amplification product in a reaction. By recording the amount of fluorescence emission at each cycle, it is possible to monitor the amplification reaction during exponential phase where the first significant increase in the amount of amplified product correlates to the initial amount of target template. The higher the starting copy number of the nucleic acid target, the sooner a significant increase in fluorescence is observed.

In some embodiments, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the DNA sequence of interest and in this way can detect the presence, and/or amount of the target nucleic acid in a sample. In some embodiments, the fluorescently-labeled DNA probes used to identify amplification products have spectrally distinct emission wavelengths, which allow them to be distinguished within the same reaction tube, for example in multiplex reactions. For example, multiplex reactions permit the simultaneous detection of the amplification products of two or more target nucleic acids, such as a control nucleic acid.

In some embodiments, a probe specific for the target nucleic acid is detectably labeled, either with an isotopic or non-isotopic label; in alternative embodiments, the amplified target nucleic acid is labeled. The probe can be detected as an indicator of the target nucleic acid species, e.g., an amplified product of the target nucleic acid species. Non-isotopic labels can, for instance, comprise a fluorescent or luminescent molecule, or an enzyme, co-factor, enzyme substrate, or hapten. The probe can be incubated with a single-stranded or double-stranded preparation of RNA, DNA, or a mixture of both, and hybridization determined. In some examples, the hybridization results in a detectable change in signal, such as in increase or decrease in signal, for example from the labeled probe. Thus, detecting hybridization can include detecting a change in signal from the labeled probe during or after hybridization relative to signal from the label before hybridization.

In some methods, the amplified product may be detected using a flow strip. In some embodiments, one detectable label produces a color and the second label is an epitope which is recognized by an immobilized antibody or antibody fragment. A product containing both labels will attach to an immobilized antibody and produce a color at the location of the immobilized antibody. An assay based on this detection method may be, for example, a flow strip (dip stick) which can be applied to the whole isothermal amplification reaction. A positive amplification will produce a band on the flow strip as an indicator of amplification of the target nucleic acid, while a negative amplification would not produce any color band.

In some embodiments, the amount (e.g., number of copies) of a target nucleic acid can be approximately quantified using the methods disclosed herein. For example, a known quantity of the target nucleic acid can be amplified in a parallel reaction and the amount of amplified product obtained from the sample can be compared to the amount of amplified product obtained in the parallel reaction. In some embodiments, several known quantities of the target nucleic acid can be amplified in multiple parallel reactions and the amount of amplified product obtained from the sample can be compared to the amount of amplified product obtained in the parallel reactions. Assuming that the target nucleic acid in the sample is similarly available to the reaction components as the target nucleic acid in the parallel reactions, the amount of target nucleic acid in the sample can be approximately quantified using these methods.

The reaction components for the methods disclosed herein can be supplied in the form of a kit for use in the detection of a target nucleic acid. In such a kit, an appropriate amount of one or more reaction components is provided in one or more containers or held on a substrate (e.g., by electrostatic interactions or covalent bonding). A nucleic acid probe and/or primer specific for a target nucleic acid may also be provided. The reaction components, nucleic acid probe, and/or primer can be suspended in an aqueous solution or as a freeze-dried or lyophilized powder, pellet, or bead, for instance. The container(s) in which the components, etc. are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in detection of target nucleic acids. In some embodiments, the kits can further include instructions to use the components in any of the methods described herein, e.g., a method using a crude matrix without nucleic acid extraction and/or purification.

In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly.

The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

EXAMPLES

Example 1

Amplification Reactions with EGTA

NEAR amplifications were performed under hot start conditions with or without the pH dependent chelating agent EGTA. Assays were set up using 0 or 100 copies of purified influenza A viral RNA and 150 nM forward template, 250 nM reverse template, and 200 nM molecular beacon probe. The sequences of the templates and molecular beacon probe were as follows: forward template, 5'-AGACTCCACACG-GAGTCTACTGACAGCCAGACA-3' (SEQ ID NO: 1); reverse template, 5'-AGACTCCATATGGAGTCTT-GATGGCCATCCGAA' (SEQ ID NO: 2); and molecular beacon probe, 5'-6-Fam-CTGGTAGCCAGGCA GCGACCAG-BHQ1-3' (SEQ ID NO: 3). The reactions were carried out under the following conditions: 100 mM Tris-Cl (pH7.9 at 20° C.), 15 mM $Na_2SO_4$, 15 mM $(NH_4)_2 SO_4$, 15 mM $MgSO_4$, 14 mM EGTA, 1 mM DTT, 0.1% Triton X-100, 0.3 mM of each dNTP, 19.2 U Bst DNA polymerase, and 15 U Nt.BstNBI nicking enzyme. The components of the assay were combined at room temperature and maintained at room temperature for about 20 minutes, following which the reactions were placed at 56° C. The reactions were monitored for 10 minutes using real-time fluorescence. Amplification was observed only in the reactions that included both EGTA and 100 copies of viral RNA (FIG. 1).

This example demonstrates that inclusion of a temperature sensitive buffer and a pH-dependent chelating agent in an amplification reaction improves amplification under hot start conditions.

Example 2

Amplification with EGTA and Lyophilized Components

Figure 2:
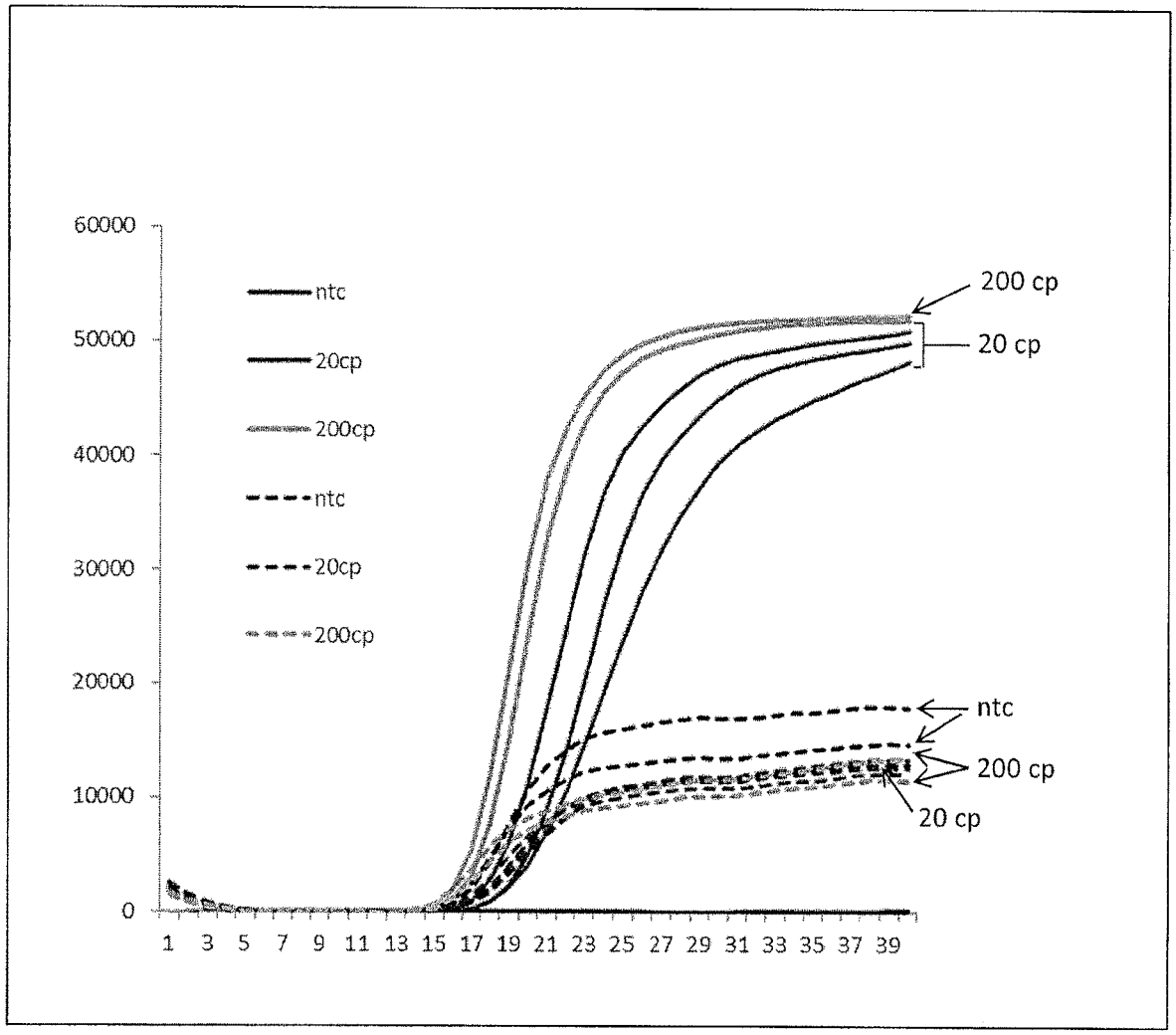
FIG. 2 is a graph depicting fluorescence of NEAR reactions containing no template (ntc), 20 copies of template (20 cp), and 200 copies of template (200 cp), in all cases with EGTA. The solid lines are Rox-labeled molecular beacon fluorescence data and the hashed lines are SyBr II fluorescence data.

NEAR reactions were performed under hot start conditions using lyophilized components. To lyophilized reaction pellets, 50 µL, of reconstitution buffer containing 50 mM Tris-HCl (pH 7.75 at 20° C.), 15 mM $(NH_4)_2SO_4$, 15 mM $MgSO_4$, and 15 mM EGTA were added. The components from lyophilized pellets included 50 nM forward template, 750 nM reverse template, 300 nM molecular beacon probe, 50 mM trehalose, 225 mM mannitol, 50 mM Tris-HCl (pH 8.5 at 20° C.), 1 mM DTT, 5 mM $Na_2SO_4$, 0.1% Triton X-100, 0.3 mM of each dNTP, 0.2×SYBR Green 1,120 U Manta DNA polymerase, and 15 U Nt.BstNBI nicking enzyme in 50 µL, after reconstitution. The sequences of the templates and molecular beacon probe were as follows: forward template, 5'-CGACTCCATATGGA GTCCTCGTCAGACCCAAAA-3' (SEQ ID NO: 4), reverse template, 5'-TGACTCCATATGGAGTCT-CATCTTTCCGTCCCC-3' (SEQ ID NO: 5), and molecular beacon, 5'-Rox-TCGGGGCAGACCCAAAACCCGA-BHQ2-3' (SEQ ID NO: 6). Amplification was performed using 20 or 200 copies of genomic DNA from *Mycobacterium bovis* BCG (ATCC strain 190115). The mixtures were held at room temperature for 15 minutes. Following the room temperature incubation, the reactions were shifted to 56° C., and the reaction was monitored for 40 minutes using real-time fluorescence. When EGTA was present in the reactions, significant amplification was observed using 20 or 200 copies of template DNA as compared to the control with no template (FIG. 2).

This example demonstrates that, under hot start conditions, inclusion of a temperature sensitive buffer and a pH-dependent chelating agent in an amplification reaction permitted amplification.

Other Embodiments

A number of embodiments of the invention have been described. Nevertheless, it will be understood that various modifications may be made without departing from the spirit and scope of the invention. Accordingly, other embodiments are within the scope of the following claims.

---

What is claimed is:

1. A method comprising:
   (a) combining a polynucleotide and an amplification reagent mixture at a first temperature between 10° C. and 30° C. to form a reaction mixture, wherein the amplification reagent mixture comprises a polymerase, magnesium ions, a temperature-sensitive buffer, and a multidentate pH-sensitive chelating agent, wherein the ratio of the multidentate pH-sensitive chelating agent concentration to the magnesium ion concentration is from about 0.5 to about 2;
   (b) adjusting the temperature of the reaction mixture from
      (i) said first temperature at which the pH of the temperature-sensitive buffer is operable for the pH-sensitive chelating agent to reversibly bind free magnesium ions in solution, such that amplification of the polynucleotide is inhibited, to
      (ii) a second temperature between 40° C. and 70° C. at which the pH of the temperature-sensitive buffer is operable to release bound magnesium ions from the pH-sensitive chelating agent, such that amplification of the polynucleotide can proceed; and
   (c) amplifying the polynucleotide at said second temperature without repeated cycling of the temperature of the reaction mixture between the first temperature and the second temperature.

2. The method of claim 1, wherein the reaction mixture comprises a free magnesium ion concentration at the first temperature that is between about 0 and about 10 mM.

3. The method of claim 1, wherein the reaction mixture comprises a free magnesium ion concentration at the first temperature that is between about 0 and about 5 mM.

4. The method of claim 1, wherein the reaction mixture comprises a free magnesium ion concentration at the first temperature that is between about 0 and about 2 mM.

5. The method of claim 1, wherein the reaction mixture comprises a free magnesium ion concentration at the first temperature that is between about 0 and about 1 mM.

6. The method of claim 1, wherein the reaction mixture comprises a free magnesium ion concentration at the first temperature that is between about 0 and about 0.2 mM.

7. The method of claim 1, wherein the reaction mixture comprises a free magnesium ion concentration at the first temperature that is between about 0 and about 0.1 mM.

8. The method of claim 1, wherein the reaction mixture comprises a free magnesium ion concentration at the second temperature that is between about 5 mM and about 50 mM.

9. The method of claim 1, wherein the reaction mixture comprises a free magnesium ion concentration at the second temperature that is between about 10 mM and about 50 mM.

10. The method of claim 1, wherein the reaction mixture comprises a free magnesium ion concentration at the second temperature that is between about 10 mM and about 20 mM.

11. The method of claim 1, wherein the reaction mixture comprises a free magnesium ion concentration at the second temperature that is between about 5 mM and about 20 mM.

12. The method of claim 1, wherein the reaction mixture comprises a free magnesium ion concentration at the second temperature that is between about 5 mM and about 10 mM.

13. The method of claim 1, wherein the multidentate pH-sensitive chelating agent is selected from the group consisting of ethyleneglycol-bis(2-aminoethylether) tetraacetic acid, EGTA derivatives, and EDTA derivatives.

14. The method of claim 1, wherein the pKa of the temperature-sensitive buffer at the second temperature is at least 0.4 less than the pKa of the temperature-sensitive buffer at the first temperature.

15. The method of claim 1, wherein the temperature-sensitive buffer comprises tris(hydroxymethyl)aminomethane.

16. The method of claim 1, wherein the first temperature is between 10° C. and about 20° C. or between about 20° C. and 30° C.

17. The method of claim 1, wherein the first temperature is between about 20° C. and 30° C.

18. The method of claim 1, wherein the second temperature is between 40° C. and about 50° C., between about 50° C. and about 60° C., or between about 60° C. and 70° C.

19. The method of claim 1, wherein the second temperature is between about 60° C. and 70° C.

20. The method of claim 1, wherein the amplification reagent mixture comprises a nicking endonuclease.

21. The method of claim 1, wherein the amplification reagent mixture comprises a DNA polymerase or an RNA polymerase.

22. The method of claim 1, wherein the amplification reagent mixture comprises a reverse transcriptase.

23. The method of claim 1, wherein the amplification reagent mixture comprises:
   (1) a first oligonucleotide comprising a 5' portion that comprises a nicking site and that is non-complementary to a target sequence of the polynucleotide and a 3' portion that hybridizes to the target sequence of the polynucleotide; and
   (2) a second oligonucleotide comprising a 5' portion that comprises a nicking site and that is non-complementary to the target sequence of the polynucleotide and a 3' portion that hybridizes to the target sequence of the polynucleotide.

24. The method of claim 1, wherein amplification of the polynucleotide occurs under substantially isothermal conditions.

25. The method of claim 1, wherein the polynucleotide is not denatured prior to combining with the amplification reagent mixture.

26. The method of claim 1, further comprising:
(d) detecting amplified polynucleotides.

27. The method of claim 1, wherein one or more components of the amplification reagent mixture is provided in a container suitable for use in a fluidic device, cartridge, or lateral flow device.

28. A method comprising:
(a) combining a polynucleotide and an amplification reagent mixture at a first temperature between 10° C. and 30° C. to form a reaction mixture, wherein the amplification reagent mixture comprises a polymerase, magnesium ions, a temperature sensitive buffer, and a multidentate pH-sensitive chelating agent selected from the group consisting of EDTA, EDTA derivatives, EGTA, and EGTA derivatives, wherein the ratio of the multidentate pH-sensitive chelating agent concentration to the magnesium ion concentration is from about 0.5 to about 2;
(b) adjusting the temperature of the reaction mixture from
(i) said first temperature at which the pH of the temperature-sensitive buffer is operable for the multidentate pH-sensitive chelating agent to reversibly bind free magnesium ions from solution, such that amplification of the polynucleotide is inhibited, to
(ii) a second temperature between 40° C. and 70° C. at which the pH of the temperature-sensitive buffer is operable to release bound magnesium ions from the multidentate pH-sensitive chelating agent to solution, such that amplification of the polynucleotide can proceed; and
(c) amplifying the polynucleotide at said second temperature.

* * * * *

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial
<220> FEATURE:
<223> OTHER INFORMATION: amplification template

<400> SEQUENCE: 1
agactccaca cggagtctac tgacagccag aca                            33

<210> SEQ ID NO 2
<211> LENGTH: 33
<212> TYPE: DNA
<213> ORGANISM: Artificial
<220> FEATURE:
<223> OTHER INFORMATION: amplification template

<400> SEQUENCE: 2
agactccata tggagtcttg atggccatcc gaa                            33

<210> SEQ ID NO 3
<211> LENGTH: 24
<212> TYPE: DNA
<213> ORGANISM: Artificial
<220> FEATURE:
<223> OTHER INFORMATION: molecular beacon probe

<400> SEQUENCE: 3
ctggtagcca ggcagcgacc agbh                                      24

<210> SEQ ID NO 4
<211> LENGTH: 33
<212> TYPE: DNA
<213> ORGANISM: Artificial
<220> FEATURE:
<223> OTHER INFORMATION: amplification template

<400> SEQUENCE: 4
cgactccata tggagtcctc gtcagaccca aaa                            33

<210> SEQ ID NO 5
<211> LENGTH: 33
<212> TYPE: DNA
<213> ORGANISM: Artificial
<220> FEATURE:
<223> OTHER INFORMATION: amplification template

<400> SEQUENCE: 5
```

```
tgactccata tggagtctca tctttccgtc ccc                                    33
```

<210> SEQ ID NO 6
<211> LENGTH: 23
<212> TYPE: DNA
<213> ORGANISM: Artificial
<220> FEATURE:
<223> OTHER INFORMATION: molecular beacon probe

<400> SEQUENCE: 6

```
tcggggcaga cccaaaaccc cga                                               23
```